(12) United States Patent
Hatley

(10) Patent No.: US 10,265,539 B2
(45) Date of Patent: Apr. 23, 2019

(54) THERAPEUTIC LED SYSTEM FOR A HOT TUB

(71) Applicant: LPI, Inc., Johnson City, TN (US)

(72) Inventor: David E. Hatley, Gray, TN (US)

(73) Assignee: LPI, Inc., Johnson City, TN (US)

( * ) Notice: Subject to any disclaimer, the term of this patent is extended or adjusted under 35 U.S.C. 154(b) by 199 days.

(21) Appl. No.: 15/407,081

(22) Filed: Jan. 16, 2017

(65) Prior Publication Data

US 2017/0232268 A1   Aug. 17, 2017

Related U.S. Application Data

(63) Continuation-in-part of application No. 14/266,312, filed on Apr. 30, 2014, now abandoned, and a continuation-in-part of application No. 14/693,467, filed on Apr. 22, 2015, now abandoned, which is a continuation-in-part of application No. 14/266,312, filed on Apr. 30, 2014, now abandoned.

(60) Provisional application No. 61/817,641, filed on Apr. 30, 2013, provisional application No. 61/982,539, filed on Apr. 22, 2014.

(51) Int. Cl.
*A61N 5/06* (2006.01)
*A61H 33/00* (2006.01)

(52) U.S. Cl.
CPC ......... *A61N 5/0618* (2013.01); *A61H 33/005* (2013.01); *A61H 33/0087* (2013.01); *A61N 5/0616* (2013.01); *A61H 2033/0083* (2013.01); *A61H 2201/0188* (2013.01); *A61H 2201/10* (2013.01); *A61H 2201/1604* (2013.01); *A61H 2201/1609* (2013.01); *A61H 2201/50* (2013.01); *A61H 2205/022* (2013.01); *A61N 2005/0642* (2013.01); *A61N 2005/0652* (2013.01); *A61N 2005/0663* (2013.01); *A61N 2005/0668* (2013.01)

(58) Field of Classification Search
CPC .......... A61H 33/005; A61H 2033/0083; A61N 5/0618; A61N 5/0616; A61N 2005/0626; A61N 2005/0642; A61N 2005/0652; A61N 2005/0663; A61N 2005/0668
USPC ......................................................... 607/90
See application file for complete search history.

(56) References Cited

U.S. PATENT DOCUMENTS

| | | | |
|---|---|---|---|
| 4,945,908 A | 8/1990 | Schneider | |
| 6,016,038 A * | 1/2000 | Mueller | H05B 33/0857 315/291 |
| 6,317,903 B1 | 11/2001 | Brunelle et al. | |
| 6,752,517 B2 | 6/2004 | Hildebrand et al. | |

(Continued)

*Primary Examiner* — Aaron F Roane
(74) *Attorney, Agent, or Firm* — Pitts & Lake, P.C.

(57) ABSTRACT

A therapeutic light emitting diode lighting system to treat seasonal affective disorder, to be provided at an upper portion of a hot tub basin above an indicated maximum water level, the hot tub basin defining at least one seat portion and corresponding headrest defined by the hot tub basin such that a facial region corresponds to the headrest, the facial region corresponding to a facial area of a person seated in the seat portion and supported by the headrest, the therapeutic light emitting diode lighting system including at least one array of light emitting diode (LED) bulbs provided on the upper area, the LED bulbs configured to illuminate colors and wavelengths selected to treat seasonal affective disorder, the LED bulbs being angled to direct light at the facial region of the hot tub body.

4 Claims, 3 Drawing Sheets

(56) References Cited

U.S. PATENT DOCUMENTS

| | | |
|---|---|---|
| 7,204,602 B2 | 4/2007 | Archer |
| 7,410,268 B2 | 8/2008 | Koren et al. |
| 7,712,913 B2 | 5/2010 | Gardenier et al. |
| 8,022,641 B2 | 9/2011 | Janik et al. |
| 8,240,873 B2 | 8/2012 | Catalano et al. |
| 2002/0030992 A1 | 3/2002 | Lefebvre et al. |
| 2003/0076692 A1 | 4/2003 | Love |
| 2006/0023454 A1 | 2/2006 | Koren |
| 2009/0083903 A1* | 4/2009 | Badiac ............... A61H 33/0087 4/541.1 |
| 2009/0222070 A1 | 9/2009 | Daffer |
| 2011/0186136 A1 | 8/2011 | Hanna et al. |

* cited by examiner

THERAPEUTIC LED SYSTEM FOR A HOT TUB

CROSS-REFERENCE TO RELATED APPLICATIONS

This Application is a continuation-in-part of U.S. patent application Ser. No. 14/266,312, filed on Apr. 30, 2014, which claims the benefit of U.S. Provisional Patent Application Ser. No. 61/817,641, filed on Apr. 30, 2013. This Application is also a continuation-in-part of U.S. patent application Ser. No. 14/693,467, filed on Apr. 22, 2015, which claims the benefit of U.S. Provisional Patent Application Ser. No. 61/982,539, filed Apr. 22, 2014, and which is a continuation-in-part of U.S. patent application Ser. No. 14/266,312, filed on Apr. 30, 2014 and already noted above. All of the foregoing applications are incorporated herein by reference in their entirety.

STATEMENT REGARDING FEDERALLY SPONSORED RESEARCH OR DEVELOPMENT

Not Applicable

FIELD OF INVENTION

The present invention relates to hot tubs and light therapy, and, more particularly, to hot tubs with light assemblies for treating symptoms of seasonal affective disorder.

BACKGROUND

Hot tubs and similar devices are used for recreation, exercise, and physical therapy. Hot tubs are often employed for treating sore muscles or for relaxation after exercise or rigorous physical activity.

Use of hot tubs often occurs out of doors and after dark. For reasons of safety and convenience, lighting systems are often mounted in hot tubs. Such lighting systems help to create a positive atmosphere or ambience, which may change as a function of the brightness of the lights, the types and colors of the lights, the number of light sources, and the location of the light sources relative to the users.

Lighting systems in hot tubs or pools have historically involved placing point light sources slightly above the water line within the main body of the tub, generally in water tight fixtures that either slightly protrude from the walls of the hot tub or pool, or, more commonly, are recessed within a niche formed into the walls to which they are mounted. Light is typically supplied from an incandescent light bulb or a light emitting diode (LED) lamp placed in the fixture.

The lighting systems in the art also generally involve one or more point light sources of varying brightness placed below the water line. These light sources propagate light into a body of water in a direction principally perpendicular to the wall on which the light source is mounted.

U.S. Pat. No. 7,712,913 discloses a lighted panel system for use in hot tubs, swim spas, and swimming pools that is mounted to the wall or lining of a tub. The lighted panel system comprises a light diffusing panel, a light source that illuminates the light diffusing panel, and a mounting structure that couples the light diffusing panel to the tub wall. Diffusers are preferably provided to the light diffusing panel in line with the light source and mounting structure to decoratively hide such components and further diffuse the light.

U.S. Pat. No. 7,204,602 discloses an LED light assembly, the light assembly comprising a reflective plate comprising a plurality of perforations formed therethrough the reflective plate, a plurality of LED bulbs wherein each LED bulb protrudes through a respective perforation of the plurality of perforations, and a control circuit selectively operable to produce a plurality of colored lights through the plurality of LED bulbs wherein the control circuit comprises a switch which when activated a defined number of times produces a plurality of at least light colors and light patterns wherein each of the plurality of at least light colors and light patterns are selected based on the defined number of times the switch is activated.

U.S. Pat. No. 6,752,517 discloses a lighting system suitable for chromatherapy includes a plurality of light fixtures mounted through walls of a tub basin to project different color light into the water in the tub. The light fixtures are operated by a central control unit and each includes a housing having a concave internal surface. An array of light emitting diodes that project different color light is mounted under a cap covering one end of the housing. A lens is threaded onto the opposite end of the housing from within the tub basin to secure the light fixture to the tub. The concave surface has the different color light projected on it, and reflects light out the light fixture in mixed fashion.

BRIEF SUMMARY

According to various example embodiments of the present general inventive concept, a hot tub housing may be provided that contains individual light therapy Light Emitting Diode bulbs that can be adjusted to illuminate up to nine different modes of different colors and different levels of nanometers designed to aid in specific medical conditions and assist in maintaining healthy skin. The bulbs may be arranged so as to be angled to a facial region that corresponds to a headrest of one or more seats formed in the hot tub basin.

Additional aspects and advantages of the present general inventive concept will be set forth in part in the description which follows, and, in part, will be obvious from the description, or may be learned by practice of the present general inventive concept.

In some example embodiments of the present general inventive concept, a hot tub with therapeutic light emitting diode lighting system for treating seasonal affective disorder includes a hot tub body with a raised area above a maximum level reached by water when the hot tub body is filled with water, and light emitting diode (LED) bulbs positioned on the raised area, the LED bulbs illuminating colors and wavelengths selected to treat seasonal affective disorder, the LED bulbs being angled to direct light at the facial region of a person sitting in the hot tub body. It is noted that while seasonal affective disorder light therapy is discussed in regard to the example embodiments in these descriptions, various other example embodiments include light therapy LED bulbs configured to treat other conditions instead of, or along with, seasonal affective disorder.

Some embodiments further include LED bulbs positioned below the raised area.

In some embodiments, the LED bulbs are capable of being adjusted to illuminate multiple wavelengths.

In some embodiments, the LED bulbs illuminate green light.

In some embodiments, the LED bulbs illuminate light that includes light with a wavelength of 552 nanometers.

In some example embodiments of the present general inventive concept, a therapeutic light emitting diode lighting system for treating seasonal affective disorder, to be installed in a hot tub wall, includes light emitting diode (LED) bulbs positioned in the hot tub wall, the LED bulbs illuminating colors and wavelengths selected to treat seasonal affective disorder, the LED bulbs being angled to direct light at the facial region of a person sitting in the hot tub body.

In some embodiments, the LED bulbs are capable of being adjusted to illuminate multiple wavelengths.

In some embodiments, the LED bulbs illuminate green light.

In some embodiments, the LED bulbs illuminate light that includes light with a wavelength of 552 nanometers.

In some example embodiments of the present general inventive concept, a therapeutic light emitting diode lighting system for installation in a hot tub wall includes a light source including light emitting diode (LED) bulbs, the LED bulbs capable of being adjusted to illuminate in up to nine different modes of different colors and different wavelengths, whereby light emitted by the LED bulbs in the different modes is adapted to aid in specific medical conditions and assist in maintaining healthy skin, and a housing to hold the LED bulbs, the housing configured to angle the LED bulbs to direct light at the facial region of a person using hot tub.

In some embodiments, the LED bulbs are capable of being adjusted to illuminate multiple wavelengths.

In some embodiments, the LED bulbs are capable of being adjusted to illuminate multiple wavelengths in nine separate modes.

In some embodiments, the LED bulbs illuminate green light.

In some embodiments, the LED bulbs illuminate red light.

In some embodiments, the LED bulbs illuminate blue light.

In some embodiments, the LED bulbs illuminate yellow light.

In some embodiments, the LED bulbs illuminate light that includes light with a wavelength of 633 nanometers.

In some embodiments, the LED bulbs illuminate light that includes light with a wavelength of 552 nanometers.

In some embodiments, the LED bulbs illuminate light that includes light with a wavelength of 419 nanometers.

Other features and aspects may be apparent from the following detailed description, the drawings, and the claims.

BRIEF DESCRIPTION OF THE SEVERAL VIEWS OF THE DRAWING FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of various example embodiments, with reference to the accompanying drawings in which:

Figure 1:
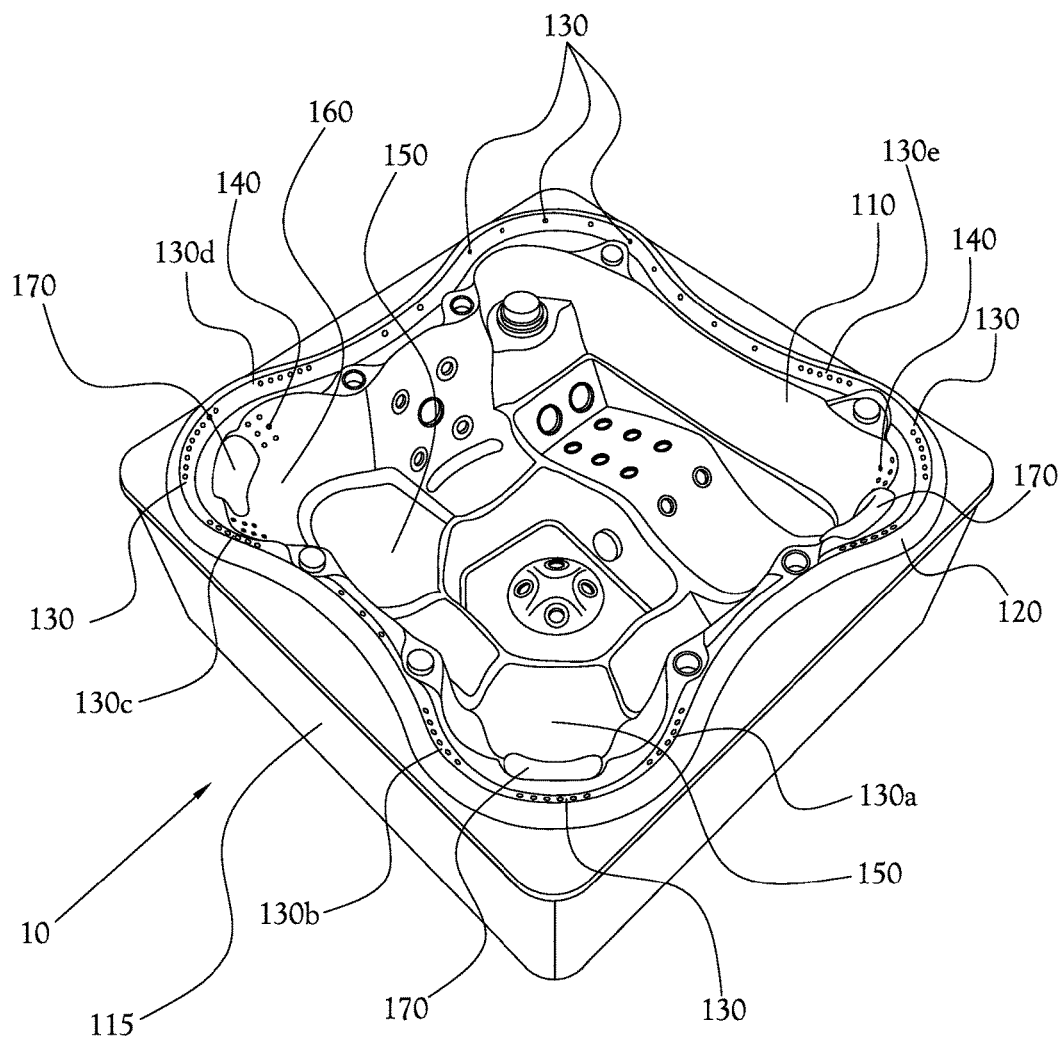
FIG. 1 illustrates a hot tub according to an example embodiment of the present general inventive concept.
Figure 3:
Figure 4:
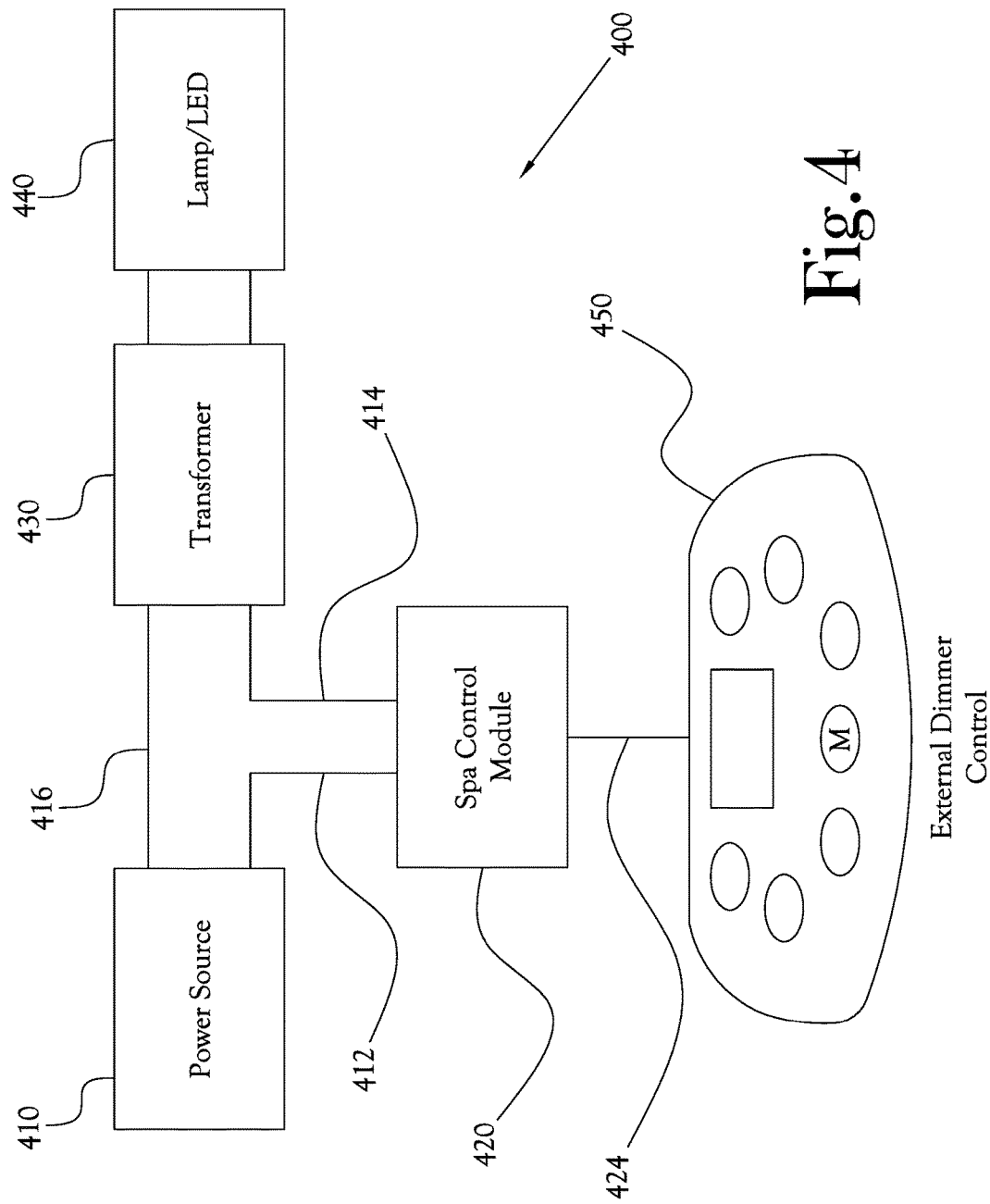

FIG. 3 illustrates another angle of a close-up view of the portion of the hot tub body illustrated in FIG. 1 according to an example embodiment of the present general inventive concept, showing a person using the hot tub and the LED bulbs directing therapeutic light at the person's facial area; and FIG. 4 is a block diagram illustrating the relationship between several components of a system according to an example embodiment of the present general inventive concept.

DETAILED DESCRIPTION

Reference will now be made to the example embodiments of the present general inventive concept, examples of which are illustrated in the accompanying drawings, illustrations, and photographs. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be simplified and/or omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

According to various example embodiments of the present general inventive concept, a hot tub housing or basin may be provided with individual light therapy Light Emitting Diode bulbs that can be adjusted to illuminate a plurality of, e.g., up to nine, different modes of different colors and different wavelengths (levels of nanometers) designed to aid in specific medical conditions and assist in maintaining healthy skin. The bulbs may be configured in the hot tub so as to be angled to a facial region that corresponds to a headrest of one or more seats formed in the hot tub basin. It is understood that while the example embodiments described below refer to hot tub application, the present general inventive concept may be provide in several other types of systems, such as a whirlpool bathtub.

In some embodiments, a therapeutic light emitting diode lighting system provided in a hot tub wall may include a light source comprising light emitting diode (LED) bulbs, the LED bulbs capable of being adjusted to illuminate in up to nine different modes of different colors and different wavelengths, whereby light emitted by the LED bulbs in the different modes is adapted to aid in specific medical conditions and assist in maintaining healthy skin, and a housing to hold the LED bulbs, the housing configured to angle the LED bulbs to direct light at the facial region of a person using the lamp.

In some embodiments, a therapeutic light emitting diode lighting system is installed in a raised molded area slightly above the main body of the hot tub, designed so that the lights are substantially at face level so that therapeutic lighting is directed at the facial areas of persons using the tub.

FIG. 1 illustrates a hot tub according to an example embodiment of the present general inventive concept. As illustrated in FIG. 1, a hot tub 10 includes a molded tub body or basin 110 which may be configured with indicia to indicate a fill line, or recommended maximum level, to which water should be filled in the basin 110. The basin 110 will typically be formed with several apertures above and below the fill line to receive water jets, button controls, lights, etc. As illustrated in FIG. 1, an outer casing 115 is provided to substantially encase the hot tub at areas other than the open basin 110, with pumps, plumbing, control lines, etc., provided between the casing 115 and the basin 110. In various example embodiments of the present general inventive concept, the basin 110 will include a raised area or lip 120 that extends above top of the outer casing 115 to help prevent water from running over the top of the basin 110, to include componentry such as lights, and/or to form portions of user accommodations. In the example embodiment illustrated in FIG. 1, a plurality of LED bulbs 130 are provides at various locations around the lip 120 to direct light inward toward the basin 110 area of the hot tub 10. Various ones of the LED bulbs 130 are light therapy bulbs that are arranged so as to shine toward particular locations corresponding to user accommodations, which will be discussed in more detail below. In various example embodiments of the present general inventive concept in which such a lip is not provided to the basin 110, the light therapy bulbs may simply be provided above the water fill line of the basin 110. In various example embodiments, a plurality of LED bulbs 140 may also be provided at various locations below the water fill line of the basin 110, or above the water fill line 140 but at locations lower than that of the LED bulbs 130.

As illustrated in FIG. 1, the hot tub basin 110 is configured so as to form a plurality of seats 150 for users of the hot tub 10. In the example embodiment illustrated in FIG. 1, three such seats 150 are illustrated; two being in two respective corners facing the center area of the hot but basin 110, and one being in a corner facing an adjacent corner ad providing a reclining position. It is understood that various example embodiments of the present general inventive concept may be utilized in hot tubs having more or fewer numbers of seats 150. As illustrated in FIG. 1, a backrest 160 portion may be provided above the back of the seat 150, and a headrest 170 portion may be provided above the backrest 160 to support a user's head when positioned in the seat 150. It is understood that the term "headrest" may refer to a structure that is at least visually differentiated from neighboring portions of the basin 110, and which may provide support to the user's head by contacting the head, neck, or a combination thereof. In various example embodiments, the headrest 170 may be padded to provide additional comfort. In various example embodiments, the headrest 170 may be contoured to provide comfort and to align the user's head in a more proper position for rest and/or light therapy. In various example embodiments, the headrest 170 may be modular, and may be selectively removable from the basin 110. The seat 150 and headrest 170 generally define a facial region which is a space that is generally occupied by the face of the user when sitting in the seat 150 with his or her head accommodated in the headrest 170.

As previously described, the LED bulbs 130 may be configured to provide light therapy to a user of the hot tub 10. In the example embodiment of the present general inventive concept illustrated in FIG. 1, each of the seats 150 is provided with an array of LED bulbs 130 to provide light therapy light that is aimed at a facial region corresponding to the respective seats 150. For example, the headrest 160 of the lowermost seat 150 of FIG. 1 is provided with an array of LED bulbs 130a,130b respectively provided proximate each side of the headrest 160. Likewise, the headrest 170 of the leftmost seat 150 is also provided with two arrays of LED bulbs 130c,130d in the same arrangement. The headrest 170 of the rightmost seat 150 of FIG. 1 is only provided with one array of the light therapy LED bulbs 130e, due to the configuration of the reclining seat facing an adjacent corner of the hot tub 10. In various example embodiments, more or fewer seats may be provided with the light therapy LED bulbs, and each seat may be respectively provided with one, two, or more LED arrays provided at angles configured to aim the therapy light at the corresponding facial regions of the seats. The light therapy LED bulbs may be provided on the lip 120 as illustrated in FIG. 1, or otherwise be provided at other locations above the water fill line. In various example embodiments, the raised area 120 and the grouping of LED bulbs 130 may be a few inches above the water fill line of the hot tub 10 when the hot tub 10 is filled with water to the designed maximum capacity of the particular model of hot tub 10. In various example embodiments, the additional grouping of LED bulbs 140 may be positioned on the molded tub body 110 below the above-mentioned grouping on LED bulbs 130 positioned on the raised area 120, and may also be light therapy bulbs angled toward the facial region of the proximate headrest 170.

Figure 2:
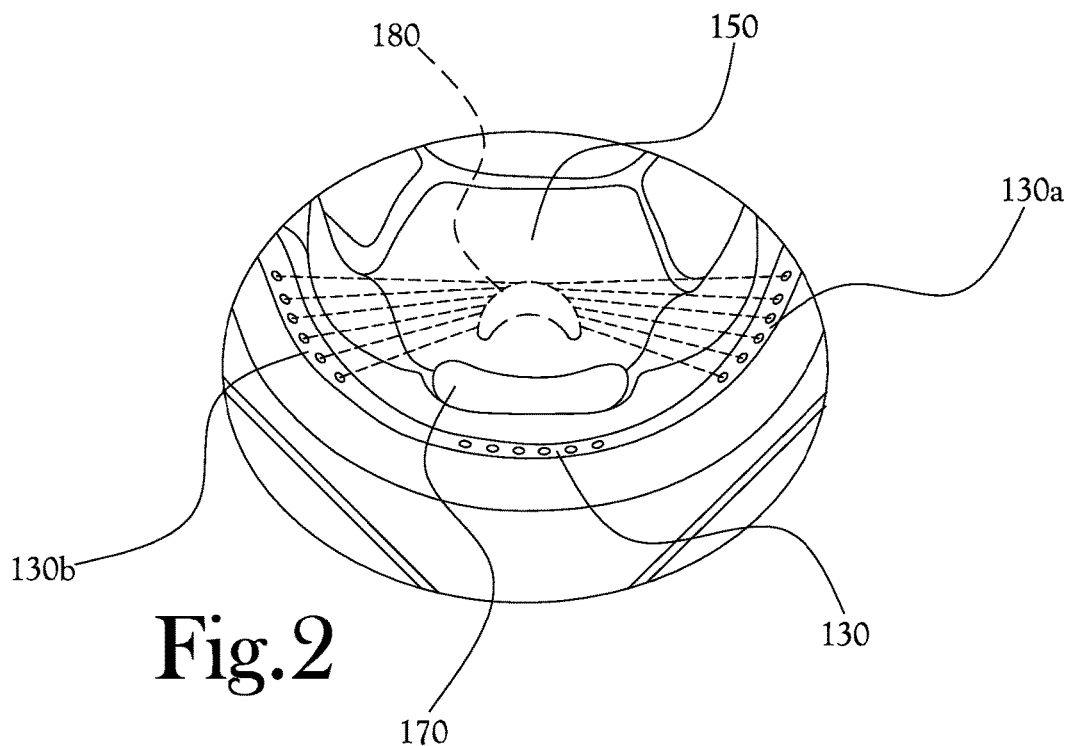
FIG. 2 illustrates a close-up view of a portion of the hot tub body of FIG. 1 proximate a headrest provided in the hot tub according to an example embodiment of the present general inventive concept.

FIG. 2 illustrates a close-up view of a portion of the hot tub body of FIG. 1 proximate a headrest provided in the hot tub according to an example embodiment of the present general inventive concept. The seat portion illustrated in FIG. 2 is the portion of the hot tub 10 having the lowermost seat 150 in FIG. 1. As previously described, the headrest 170 of FIG. 2 corresponds to a seat 150 defined by the hot tub basin 110, and a facial region 180 is defined by the placement of the head rest 170. In FIG. 2, the area 180 formed by the dashed line simply indicates an abstract expression of the general facial region associated with the headrest 170. In various example embodiments, such a facial region 180 may be defined as several inches above and forward of the headrest 170, at an area at which the face of a typical user would likely be located when using the headrest 170. As illustrated in FIG. 2, the LED bulbs 130a,130b are configured at an angle such that the light emitted from the respective bulbs is directed to the facial region 180. Whereas lights in a typical hot tub application may simply be directed perpendicularly to the wall of the basin 110, the LED bulbs 130a,130b are all aimed at the facial region corresponding to the most proximate headrest 170. As illustrated in FIG. 2, different ones of the LED bulbs 130a,130b may be provided at different angles relative to the hot tub basin 110 so as to compensate for different positions, distances, etc., relative to the facial region 180. In various example embodiments, different ones of the LED bulbs 130a,130b may also be provided at different angles in a vertical direction so as to provide more coverage from a top to a bottom of the facial region 180, along with the different horizontal angles illustrated in FIG. 2. The LED bulbs 130 provided behind the headrest 170 may also be light therapy bulbs aimed at regions of the back of the head, according to various example embodiments of the present general inventive concept, or may simply be ornamental.

FIG. 3 illustrates another angle of a close-up view of the portion of the hot tub body illustrated in FIG. 1 according to an example embodiment of the present general inventive concept, showing a person using the hot tub and the LED bulbs directing therapeutic light at the person's facial area. The portion of the hot tub 10 illustrated in FIG. 3 is the same as that illustrated in FIG. 2, except shown from the front of the headrest 170 and with a user of the hot tub 10 positioned in the seat 150. As illustrated in this example embodiment, the headrest 170 provides support at the neck and lower head regions of the user, and the LED bulb arrays 130a,130b are aimed at the facial region associated with the headrest 170, which is generally occupied by the face of the user in the seat 150. Angling the LED bulbs 130a,130b to be aimed at such a facial region provided more comprehensive coverage to the facial area, and thus more effective therapy. In various example embodiments, the respective arrays 130a,130b may be selectively controlled to provide different levels or types of therapy to different sides of the face, or to provide therapy to only one side of the face, according to the wishes or needs of the user. In various example embodiments of the present general inventive concept, the LED arrays may be provided in a housing that is provided to the hot tub basin 110, or in adhesive strips that may be affixed to the hot tub basin 110. In various example embodiments of the present general inventive concept, LED arrays which are added to an existing hot tub basin 110 may be selectively battery powered, and may include a watertight battery compartment for providing power to the LED arrays. In various example embodiments of the present general inventive concept, the individual LED bulbs provided in such housings and/or strips may be configured to be adjustable so as to be selectively angled to the facial region after the at least one array of LED bulbs is provided to the hot tub basin.

In various example embodiments of the present general inventive concept, a therapeutic LED bulb system is capable of nine different modes, including:

Mode 1: emitting red light at approximately 633 nanometers for aid in collagen and anti-aging.

Mode 2: emitting blue light at approximately 419 nanometers for aid in Acne treatment.

Mode 3: emitting green light at approximately 552 nanometers for aid in treatment for seasonal affective disorder (SAD).

Mode 4: emitting normal red light only intended for illumination.

Mode 5: emitting normal blue light only intended for illumination.

Mode 6: emitting normal yellow light only intended for illumination.

Mode 7: emitting normal green light only intended for illumination.

Mode 8: emitting white light only intended for illumination.

Mode 9: emitting normal red, blue, yellow, green, white light in a sequence of one color after the other intended only for illumination.

Thus, in various embodiments of the present general inventive concept, the LED bulbs can be adjusted to illuminate different colors and different wavelengths, with at least some of the colors and wavelengths being selected and designed to aid in specific medical conditions (such as Seasonal Affective Disorder) or to assist in maintaining healthy skin.

In various example embodiments of the present general inventive concept, a system may be provided that electronically connects LED perimeter lights installed around the upper inward-facing wall of a hot tub or whirlpool bathtub to an external or topside control panel, allowing an occupant or user of the hot tub or whirlpool bathtub to dim or brighten the LED lights utilizing a button or dimmer switch on the topside control panel. Such a system (hereinafter a "dimmer switch control system") may be employed, for example, in a housing containing individual light therapy LED bulbs as discussed in reference to FIGS. 1-3, and which can be adjusted to illuminate up to nine different modes of different colors and different wavelengths designed to aid in specific medical conditions and assist in maintaining healthy skin.

In various example embodiments, a therapeutic light emitting diode lighting system for installation in a hot tub wall includes a light source comprising one or more arrays light emitting diode (LED) bulbs 130 capable of being adjusted to illuminate in up to nine different modes of different colors and different wavelengths, whereby light emitted by the LED bulbs in the different modes is adapted to aid in specific medical conditions and assist in maintaining healthy skin, and a housing to hold the LED bulbs, the housing configured to angle the LED bulbs to direct light at the facial region of a person using the lamp.

FIG. 4 is a block diagram illustrating generally a control system 400 for a therapeutic light emitting diode lighting assembly. As illustrated in the example embodiment of FIG. 4, the system may include a power source 410, a spa control module 420, and a transformer 430 connected to a light source 440, generally an LED array or a lamp or some similar light element. The spa control module 420 is connected by power lines 412, 414 to the power source 410 and the transformer 430, respectively. The power source 410 and the transformer 430 also share a direct connection 416. The spa control module 420 may be connected 424 to an external control panel 450, which includes controls configured to adjust the intensity and/or frequency of light emitted by the light source 440. The spa control module 420 accepts user commands entered into the external control panel 450, and the spa control module 420 then adjusts the power and/or signals flowing to the transformer 430 and thence to light source 440.

In various example embodiments, a therapeutic light emitting diode lighting system may be installed in a raised molded area slightly above the main body of the hot tub, designed so that the lights are substantially at face level so that therapeutic lighting is directed at the facial regions corresponding to seating portions defined by the hot tub basin, and therefore to the facial areas of persons using the tub. As previously discussed in regard to FIGS. 1-3, the lights may be provided at angles so as to be aimed at the facial regions In some embodiments, a molded manifold for installation into the plumbing water line in a hot tub or whirlpool bathtub is fabricated from PVC or a similar polymer material.

Turning specifically to the dimmer switch control system, in various example embodiments the system may be wired and programmed into a main control pack that is used to operate every other function of the hot tub or whirlpool bathtub. Thus the occupant can use the same topside control to adjust the lighting level. In varioius example embodiments, variable settings for the perimeter LED lighting controlled by the dimmer switch control system range from "off" to the highest intensity setting capable for the particular LED components in use.

According to various example embodiments of the present general inventive concept, a hot tub with a therapeutic light emitting diode lighting system for treating seasonal affective disorder is provided, the hot tub including a hot tub basin with an upper area above an indicated maximum water level of the hot tub basin, at least one seat portion and corresponding headrest defined by the hot tub basin such that a facial region corresponds to the headrest, the facial region corresponding to a facial area of a person seated in the seat portion and supported by the headrest, and at least one array of light emitting diode (LED) bulbs provided on the upper area, the LED bulbs configured to illuminate colors and wavelengths selected to treat seasonal affective disorder, the LED bulbs being angled to direct light at the facial region of the hot tub body. One or more of the LED bulbs may configured at different angles from the remaining LED bulbs such that the entire array of LED bulbs are aimed at the facial region. The different angles may vary in vertical and/or horizontal components of a direction from the respective LED bulbs to the facial region. The at least one array of LED bulbs may be provided adjacent to the headrest. Two arrays of LED bulbs may be provided adjacent to the head rest such that one array is provided at each side of the headrest. The upper area may be a raised area of the hot tub basin extending above a housing of the hot tub. One or more arrays of the LED bulbs may be provided below a top of the raised area. The array of LED bulbs may be configured to be selectively adjustable to illuminate multiple wavelengths. The hot tub may further include a control module for adjusting an intensity of light emitted by the at least one array of LED lights, the control module being in electronic communication with the at least one array of LED lights, and an external control panel in communication with the control module, the external control panel being in electronic communication with the control module. The external control panel may include a button and/or a dimmer switch. The LED bulbs may illuminate green light. The LED bulbs may illuminate light that includes light with a wavelength of 552 nanometers. A plurality of seat and headrest portions may be defined in the hot tub basin, and at least one of the arrays of LED bulbs may be provided to two or more of the headrest portions. The at least one of the respective arrays of LED bulbs may be provided adjacent to the headrest portions to which it corresponds.

According to various example embodiments of the present general inventive concept, a therapeutic light emitting diode lighting system is provided to treat seasonal affective disorder, the lighting system configured to be provided at an upper portion of a hot tub basin above an indicated maximum water level, the hot tub basin defining at least one seat portion and corresponding headrest defined by the hot tub basin such that a facial region corresponds to the headrest, the facial region corresponding to a facial area of a person seated in the seat portion and supported by the headrest. The therapeutic light emitting diode lighting system may include at least one array of light emitting diode (LED) bulbs provided on the upper area, the LED bulbs configured to illuminate colors and wavelengths selected to treat seasonal affective disorder, the LED bulbs being angled to direct light at the facial region of the hot tub body. The at least one array of LED bulbs may be provided in a housing to be adhered to the upper portion of the hot tub basin. The at least one array of LED bulbs may be provided in an adhesive strip to be adhered to the upper portion of the hot tub basin. The at least one array of LED bulbs may include a watertight battery compartment to power the LED bulbs. The individual LED bulbs may be configured to be adjustable in the housing so as to be selectively angled to the facial region after the at least one array of LED bulbs is provided to the hot tub basin. The therapeutic light emitting diode lighting system may include a control system for adjusting the intensity of the light emitted by the LED bulbs, the control system including a control panel with a user interface, the control panel with a user interface being provided on a top surface of the tub.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams, drawings, and photographs included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, photographs, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. A therapeutic light emitting diode lighting system to treat seasonal affective disorder, to be provided at an upper portion of a hot tub basin above an indicated maximum water level, the hot tub basin defining at least one seat portion and corresponding headrest defined by the hot tub basin such that a facial region corresponds to the headrest, the facial region being configured to accommodate a facial area of a person seated in the seat portion and supported by the headrest, comprising:

at least one array of light emitting diode (LED) bulbs provided on the upper area, the LED bulbs configured to illuminate colors and wavelengths selected to treat seasonal affective disorder, the LED bulbs being angled to direct light at the facial region of the hot tub body;

wherein the at least one array of LED bulbs are provided in a housing to be adhered to the upper portion of the hot tub basin; and wherein the individual LED bulbs are configured to be adjustable in the housing so as to be selectively angled to the facial region after the at least one array of LED bulbs is provided to the hot tub basin.

2. The therapeutic light emitting diode lighting system of claim 1, further comprising a control system for adjusting the intensity of the light emitted by the LED bulbs, the control system including a control panel with a user interface, the control panel with a user interface being provided on a top surface of the tub.

3. A therapeutic light emitting diode lighting system to treat seasonal affective disorder, to be provided at an upper portion of a hot tub basin above an indicated maximum water level, the hot tub basin defining at least one seat portion and corresponding headrest defined by the hot tub basin such that a facial region corresponds to the headrest, the facial region being configured to accommodate a facial area of a person seated in the seat portion and supported by the headrest, comprising:

at least one array of light emitting diode (LED) bulbs provided on the upper area, the LED bulbs configured to illuminate colors and wavelengths selected to treat seasonal affective disorder, the LED bulbs being angled to direct light at the facial region of the hot tub body;

wherein the at least one array of LED bulbs are provided in an adhesive strip to be adhered to the upper portion of the hot tub basin.

4. The therapeutic light emitting diode lighting system of claim 3, wherein the at least one array of LED bulbs comprise a watertight battery compartment to power the LED bulbs.

* * * * *